United States Patent [19]
Khosravi et al.

[11] Patent Number: 5,824,052
[45] Date of Patent: Oct. 20, 1998

[54] COILED SHEET STENT HAVING HELICAL ARTICULATION AND METHODS OF USE

[75] Inventors: Farhad Khosravi, San Mateo; Michael Hogendijk, Palo Alto; John Spiridigliozzi, Belmont, all of Calif.

[73] Assignee: EndoTex Interventional Systems, Inc., Cupertino, Calif.

[21] Appl. No.: 819,967

[22] Filed: Mar. 18, 1997

[51] Int. Cl.⁶ ........................................ A61F 2/06
[52] U.S. Cl. ........................ 623/1; 623/12; 623/195
[58] Field of Search ........................ 623/1, 11, 12; 606/192, 194, 195

[56] References Cited

U.S. PATENT DOCUMENTS

| | | | |
|---|---|---|---|
| Re. 34,327 | 7/1993 | Kreamer | 623/1 |
| 4,553,545 | 11/1985 | Maass et al. | 128/341 |
| 4,655,770 | 4/1987 | Wallsten | 623/1 |
| 4,665,918 | 5/1987 | Garza et al. | 128/343 |
| 4,733,665 | 3/1988 | Palmaz | 128/343 |
| 4,739,762 | 4/1988 | Palmaz | 128/473 |
| 5,007,926 | 4/1991 | Derbyshire | 623/1 |
| 5,102,417 | 4/1992 | Palmaz | 606/195 |
| 5,147,370 | 9/1992 | McNamara et al. | 606/108 |
| 5,246,445 | 9/1993 | Yachia et al. | 606/108 |
| 5,314,444 | 5/1994 | Gianturco | 606/195 |
| 5,344,426 | 9/1994 | Lau et al. | 606/198 |
| 5,421,955 | 6/1995 | Lau et al. | 216/48 |
| 5,423,885 | 6/1995 | Williams | 623/1 |
| 5,441,515 | 8/1995 | Khosravi et al. | 606/194 |
| 5,443,500 | 8/1995 | Sigwart | 623/1 |
| 5,476,505 | 12/1995 | Limon | 623/1 |
| 5,556,413 | 9/1996 | Lam | 606/198 |

Primary Examiner—Randy C. Shay
Attorney, Agent, or Firm—Fish & Neave; Nicola A. Pisano

[57] ABSTRACT

An endoprosthesis is provided having at least first and second resilient coiled sheet portions, and an intermediate region comprising a helical articulation. The coiled sheet portions may be of the same or different diameters so as to accommodate a taper in the body lumen, while the helical articulation comprises a mesh portion that provides both flexibility and high radial strength, and which contracts to its delivery profile with relatively few turns. The coiled sheet portions also may be of the same or different lengths, and for very long devices, may be interspersed between a plurality of helical articulation portions. The pitch of the helical articulation may be varied to create a partial telescoping of the helical articulation within one of the first and second coiled sheet portions when in a contracted state. The prosthesis may also be used for treating bifurcated vessels.

30 Claims, 6 Drawing Sheets

COILED SHEET STENT HAVING HELICAL ARTICULATION AND METHODS OF USE

FIELD OF THE INVENTION

The present invention relates generally to intraluminal endoprostheses, commonly referred to as "stents," for maintaining the patency of a body lumen. More specifically, the present invention is directed to providing resilient coiled sheet stents having helical articulations that enable the stents to be deployed in tortuous and irregular body lumens.

BACKGROUND OF THE INVENTION

A number of stent designs are known for use in conjunction with minimally-invasive approaches for treating vascular disease and other diseases that cause narrowing of body lumens. These endoprostheses or stents generally consist of an expandable tubular member that contacts and supports the body lumen following a dilatation procedure in which the cause of the narrowing has been treated, for example, by use a dilatation balloon or atherectomy device. It has also been suggested to use stents in conjunction with tubular grafts to treat the occurrence of aneurysm, or localized weakening, of a body lumen.

An ideal stent provides a number of mechanical characteristics, which none of the previously known stent designs provide. For example, it is desirable for a stent to have a small profile and high flexibility when in the contracted state to pass through narrow and tortuous passageways, but to have high radial strength over a range of expanded diameters, with little or no length change when deployed at the desired location. In some applications, such as deployment in the carotid arteries, is also desirable for the stent to have a high degree of elasticity, so that if it is inadvertently compressed, the stent will re-expand to its originally implanted diameter.

Balloon expandable stents, such as described in U.S. Pat. Nos. 4,733,665 and 4,739,762 to Palmaz, generally provide wire-mesh or slotted tubular members that are plastically deformed from a contracted diameter to an expanded state. Disadvantages of such stents include low flexibility when in the contracted state, a limited range of expanded diameters having adequate radial strength, and high crushability. U.S. Pat. No. 5,102,417 to Palmaz describes a stent comprising a series of slotted tubular elements connected by links that attempts to address the low flexibility aspect of the design. This stent remains unsuitable for use in body lumens subject to compression, however, because of its low crush resistance. U.S. Pat. No. 5,314,444 to Gianturco, U.S. Pat. No. 5,421,955 to Lau et al. and U.S. Pat. No. 5,556,413 to Lam describe other types of balloon expandable stents which suffer from one or more of the above-described disadvantages.

U.S. Pat. No. 4,655,771 to Wallsten provides a woven wire tubular mesh member which is contracted to its delivery profile by elongating the stent. When the ends of the stent are released, the stent attains its expanded diameter by undergoing a considerable shortening of length. Drawbacks inherent in stents of this design include a limited range of diameters at which acceptable radial strength can be achieved, and relatively low longitudinal flexibility. In addition, the considerable shortening of the stent encountered during deployment can result in a lack of precision in stent placement.

U.S. Pat. No. 5,246,445 to Yachia et al. describes a stent formed as a helical wire coil. The wire coil is drawn down onto a catheter for delivery by axially extending the catheter and is deployed by releasing one end of the stent. Like the Wallsten, the device described in the Yachia et al. patent experiences considerable longitudinal shortening during deployment. The device includes a further drawback that, as the device expands, the free end of the coil is thought to whip around the catheter at high speed. Because such behavior could dislodge pieces of plaque from the interior of the vessel wall, such stent designs appear unsuitable for use in the carotid arteries and in other vessels in which embolization presents a problem. U.S. Pat. No. 4,665,918 to Garza et al., U.S. Pat. No. 5,476,505 to Limon and U.S. Pat. No. 4,553,545 to Maass et al. describe alternative helical coil designs.

Coiled sheet stents, as described, for example, in U.S. Pat. No. Re. 34,327 to Kreamer, U.S. Pat. No. 5,007,926 to Derbyshire, U.S. Pat. No. 5,443,500 to Sigwart and U.S. Pat. No. 5,441,515 to Khosravi et al., describe stents formed of coiled sheets that include various means for locking the stents at a desired expanded diameter. Such stents attain a number of the characteristics of an ideal stent, including low delivery profile, excellent radial strength over a range of expanded diameters, no longitudinal contraction during deployment and good resistance against crushing. A drawback of such stents, however, is that they are relatively rigid when contracted to a delivery profile. Accordingly, such stents may encounter tradeoffs with respect to maximum stent length versus capability to track a tortuous vessel. In addition, it is contemplated that the edges of previously known coiled sheet stents may become misaligned when deployed in tapered lumens.

In view of the foregoing, it would be desirable to provide a stent which has a high degree of longitudinal flexibility so that it can be advanced through a tortuous body lumen and be readily expanded, yet which has high radial strength over a range of expanded diameters.

It further would be desirable to provide a stent that has a high degree of longitudinal flexibility, but which is resistant to crushing.

It also would be desirable to provide a stent that has a high degree of longitudinal flexibility, but which experiences little overall shortening during deployment.

It further would be desirable to provide a resilient stent that exhibits the high crush resistance and radial strength and may be deployed in a tapered or bifurcated body lumen.

Apart from the foregoing considerations, it frequently is desirable to use a stent to affix a graft so that it spans an aneurysm in the body vessel, for which applications previously known stents have only limited utility. In particular, for previously known stents to be effective in such applications, the portion of the lumen proximal and distal to the aneurysm (i.e., the proximal neck and the distal cuff of an aneurysm) must be relatively straight and of sufficient length to permit the stent to obtain adequate apposition on the lumen walls. If the proximal neck and/or distal cuff of an aneurysm are of insufficient length, there may be leakage at the proximal or distal ends of the graft or both, as described, for example, in T. Chuter et al., *Endoluminal Vascular Prostheses*, at pp. 22–33, Little Brown & Co. (1995).

Accordingly, it also would be desirable to provide a stent and methods for use suitable for repairing an aneurysm, or other forms of intraluminal disease, that can be used in patients having relatively short lengths of body lumen wall proximal or distal to the aneurysm.

SUMMARY OF THE INVENTION

In view of the foregoing, it is an object of the present invention to provide a stent which has a high degree of longitudinal flexibility so that the stent can be advanced through a tortuous body lumen, be readily expanded, and has high radial strength over a range of expanded diameters.

It is a further object of this invention to provide a resilient stent that has a high degree of longitudinal flexibility and high crush resistance, but which experiences little overall shortening during deployment.

It is another object of the present invention to provide a stent that may be deployed in a tapered or bifurcated body lumen.

It is another and different object of this invention to provide a stent, and methods for use, suitable for repairing an aneurysm, or other forms of intraluminal disease, that may be deployed in patients having relatively short lengths of body lumen wall proximal or distal to the aneurysm.

These and other objects of the invention are accomplished by providing a coiled sheet stent having a helical articulation, whereby the stent is flexible along its longitudinal axis to facilitate delivery through a tortuous body lumen, but provides high radial strength over a range of deployed diameters.

In accordance with the present invention, a stent is formed having at least first and second resilient coiled sheet portions, and an intermediate region comprising a helical articulation. The coiled sheet portions may be of the same or different diameters so as to accommodate a taper in the body lumen, while the helical articulation comprises a mesh portion that provides both flexibility and high radial strength, and which contracts to its delivery profile with relatively few turns. The coiled sheet portions also may be of the same or different lengths, and for very long devices, may be interspersed between a plurality of helical articulations.

Each of the coiled sheet portions at the ends of the stent preferably includes locking elements for retaining the coiled sheet at an expanded diameter. The stent may be made of a variety of materials including stainless steel, thermal shape-memory polymers or metals, super-elastic materials such as nickel-titanium alloys, or other biocompatible elastic materials such as stainless steel, tantalum, platinum and suitable tungsten alloys.

In a first family of embodiments of the present invention, the turns of the helical articulation overlap one another in a contracted state, thereby shortening the overall length of the stent during delivery, as well as providing longitudinal flexibility. When deployed, the stent has little gap between adjacent turns of the articulation, to reduce the protrusion of tissue through the gaps and lower the risk of restenosis.

In a second family of embodiments of the invention, the turns of the helical articulation do not overlap substantially when the stent is in its contracted state, so that gaps are formed between the turns of the helical portion of the stent when deployed. This family of embodiments of the present invention is particularly well suited for treatment of intraluminal disease in patients having relatively short lengths of relative straight body lumen wall proximal or distal to the intraluminal disease, such as at a bifurcation or side branch of a common body lumen. In accordance with this aspect of the present invention, two or more stents having a loose pitch in the helical articulation may be partially nested within a common body lumen while the other ends of the stents are implanted in respective separate branches of the bifurcated body lumen.

BRIEF DESCRIPTION OF THE DRAWINGS

Further features of the invention, its nature and various advantages will be more apparent from the accompanying drawings and the following detailed description of the preferred embodiments, in which.

DETAILED DESCRIPTION OF THE PREFERRED EMBODIMENTS

The present invention provides stents for treatment of intraluminal disease that overcome the limitations of previously known stents. In particular, a stent constructed in accordance with the present invention provides longitudinal flexibility to facilitate delivery through a tortuous body lumen, yet provides the high radial strength and high crush resistance associated with previously known coiled sheet stents. Stents of the present invention may also advantageously be used to treat intraluminal disease located at or near a bifurcation or side branch of a body lumen, such as at carotid artery bifurcations.

Figure 1A:
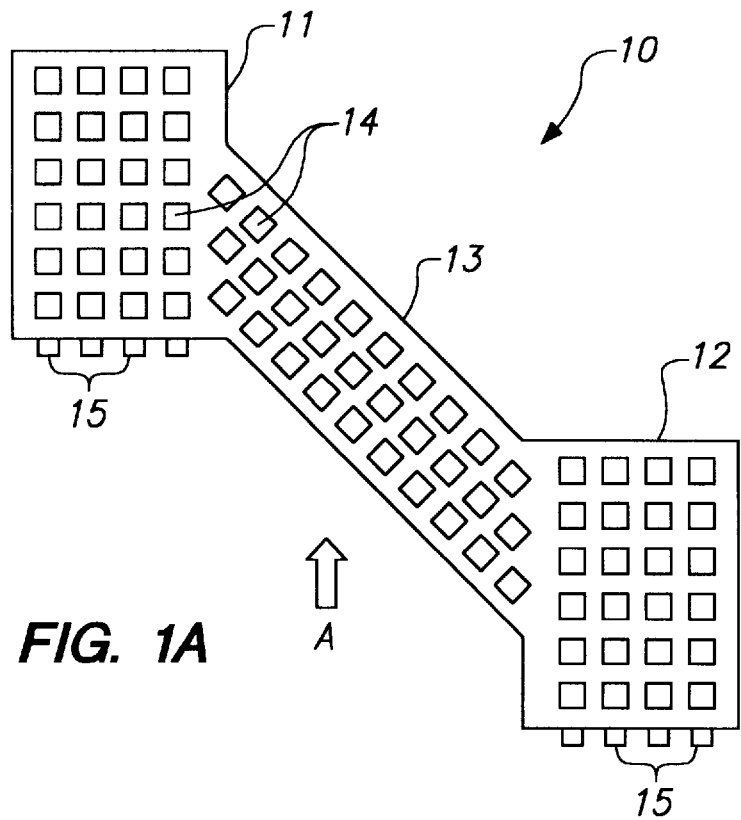
FIG. 1A is a plan view of an illustrative one of a first family of embodiments of stents constructed in accordance with present invention.

Referring to FIG. 1A, stent 10 constructed in accordance with a first family of embodiments of the present invention is described. Stent 10 comprises resilient coiled sheet portions 11 and 12 disposed at the proximal and distal ends of the stent, and at least one helical articulation 13 joining coiled sheet portions 11 and 12.

In a first family of embodiments, helical articulation 13 is configured so that its turns overlap one another and at least partially telescope within one of the coiled sheet portions 11 and 12 when the stent is rolled in direction A (as indicated in FIG. 1A). This telescoping behavior reduces the overall length of the stent, provides some flexibility at the articulation between the coiled sheet portions during delivery, and reduces the gap between adjacent turns of helical articulation 13 once deployed. In a second family of embodiments of the present invention, described in greater detail hereinafter, the helical articulation has a looser pitch that allows gaps to form between adjacent turns of the helical articulation when it is deployed.

Referring again to FIG. 1A, due to the overlapping of adjacent turns of the helical articulation, stents in the first family of embodiments of the present invention are directional. In its contracted state (and possibly in its expanded state, if so desired), one end of the stent has a greater inside diameter than the opposite end of the stent, and may have intermediate decreasing inside diameters corresponding to each turn of the helical articulation. Accordingly, it is contemplated that the stent should be delivered and implanted so that fluids passing through the lumen enter the end of the stent with the smaller inside diameter, so as to reduce turbulence and the risk of thrombosis.

Still referring to FIG. 1A, stent 10 includes multiplicity of openings 14, which enable tissue lining the wall of the body lumen to envelope the stent. Openings 14 may be square, diamond-shaped, circular, or of other shapes designed to promote regrowth of the vessel intima following, for example, a balloon dilatation procedure. Stent 10 may also include teeth 15 located on the inner edge of coiled sheet portions 11 and 12 that serve to lock the stents at a desired expanded diameter. Such locking elements are per se known in the art, as shown, for example, by Sigwart U.S. Pat. No. 5,443,500 and Derbyshire U.S. Pat. No. 5,007,926.

Stent 10 generally comprises a thin (about 2–4 mils) flat sheet of a biocompatible material, such as stainless steel, a polymer, a thermal shape-memory polymer or metal, superelastic material (such as a nickel-titanium alloy), or other biocompatible elastic material such as a tantalum, platinum or tungsten alloy. In a preferred embodiment of the present invention, the material is sufficiently resilient so that the stent at least partially expands when it is released from a delivery catheter. Stent 10 may be integrally formed having coiled sheet portions 11 and 12, helical articulation 13 and multiplicity of openings 14 by any of a number of conventional metal working processes, including die and punch, laser cutting, or chemical etching, as described, for example, in the aforementioned Khosravi and Sigwart et al. patents.

As depicted in the illustrative embodiment of FIG. 1A, coiled sheet portions 11 and 12 are approximately the same length as intermediate helical articulation 13. Accordingly, for a stent having an overall length of 2.0 cm and an expanded diameter of 7.0 mm (for example, for use in the common carotid arteries), it is contemplated that the lengths of the coiled sheet portions will be about 6 mm each, while the length of the helical articulation will be about 8 mm. As of course will be apparent to one of skill in the art, however, the lengths of the coiled sheet portions and helical articulation may be varied depending upon the intended application and desired mechanical characteristics of the stent. Moreover, the lengths of the coiled sheet portions 11 and 12 may be different from each other, as well as different from the length of the helical articulation. In addition, the number of turns in the helical articulation, as well as the width per turn of the articulation, may be varied to suit a particular application.

Figure 1B:
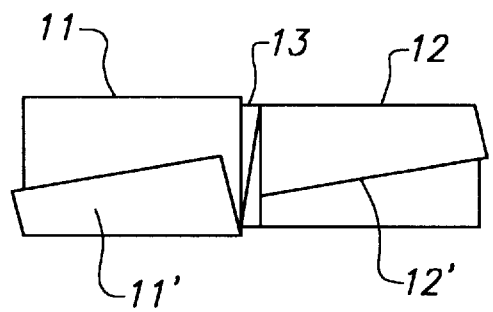
FIG. 1B is an elevation view of the stent of FIG. 1A in its contracted state.

Referring now to FIG. 1B, helical portion 13 is dimensioned so that when the stent is rolled to a small diameter, by rolling in the direction A indicated in FIG. 1A, the helical portion telescopes within the coiled sheet portions 11 and 12. In it therefore observed that the articulation improves trackability of the stent not only by providing some longitudinal flexibility, but also by reducing the overall length of the stent in its contracted state. As illustrated in FIG. 1B, free edges 11' and 12' of coiled sheet portions 11 and 12 may experience some tilting as the helical portion is wound down. Moreover coiled sheet portion 12 assumes a smaller outer diameter than coiled sheet portion 11 because of the directional nature of the stent.

Figure 1C:
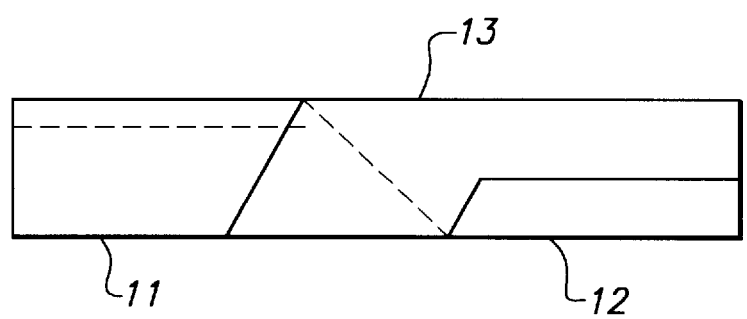
FIG. 1C is an elevation view of the stent of FIG. 1C in its expanded state.

More particularly, for a preferred embodiment of the stent made of a shape memory alloy such as a nickel-titanium alloy, a sheet of suitable material is first formed into the shape depicted in FIG. 1A. The sheet is then rolled about a mandrel in direction A (indicated in FIG. 1A) to form a tubular member having an expanded configuration as shown in FIG. 1C, and then heat treated to activate the shape memory of the material. Stent 10 is then rolled to its contracted state for delivery by twisting one end of the stent in a clockwise direction and simultaneously twisting the opposite end of the stent in a counter-clockwise direction to attain the shape illustrated in FIG. 1B.

The contracted stent is then loaded into a sheath for delivery, as described, for example, in Sigwart U.S. Pat. No. 5,443,500, Lau et al. U.S. Pat. No. 5,344,426 or Garza et al. U.S. Pat. No. 4,665,918, the entireties of which are incorporated herein by reference. In addition, a restraining member may be threaded through coiled sheet portions 11 and 12, as described, for example, in Sigwart U.S. Pat. No. 5,443,500, to prevent the stent from unwinding.

Figure 2A:
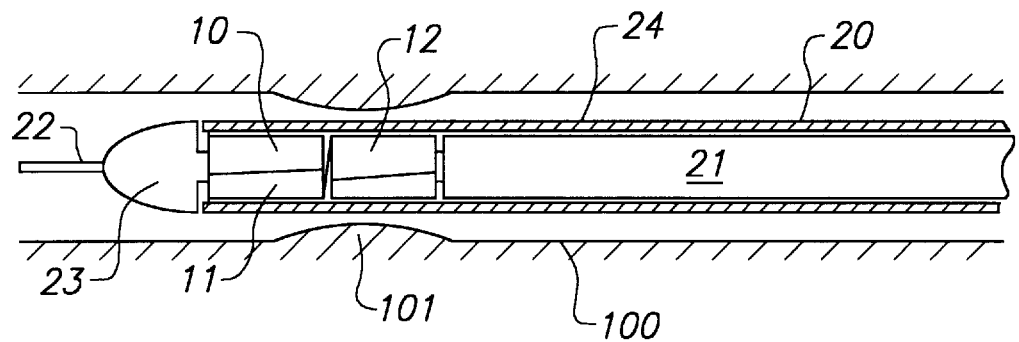
FIGS. 2A–2C are views of the steps of deploying the stent of FIGS. 1.
Figure 2B:
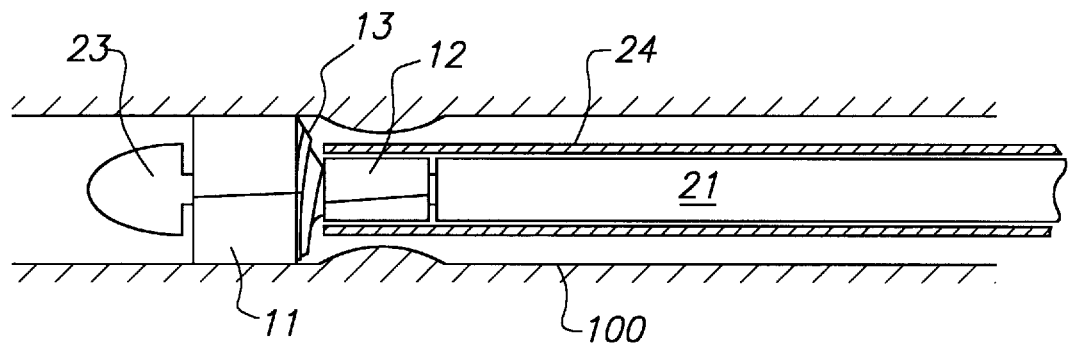
Figure 2C:
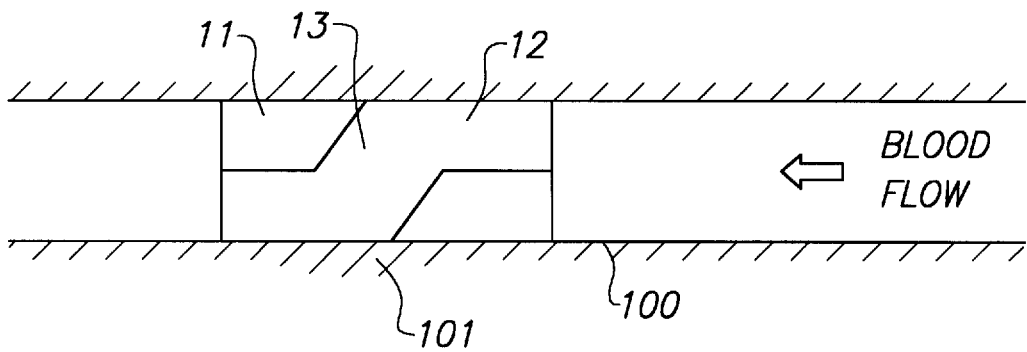

More particularly, referring to FIGS. 2A–2C, stent 10 is rolled to its contracted state and disposed within delivery system 20, such as described in the above-incorporated Garza patent. Delivery system 20 includes catheter 21 having a central lumen for accepting guide wire 22, nose cone 23 and outer sheath 24. Particular to the directional nature of stent 10, the stent is loaded into the sheath so that coiled sheet portion 11 having the larger diameter is positioned distally in catheter 21. Delivery system 20 then is inserted into body lumen 100 through a major vessel along guide wire 22, as is well-known in the art, until the distal end of the delivery system is located distally of the stenosis 101.

Once the location of the delivery system is established, for example, using fluoroscopy and standard angiographic techniques, sheath 24 of delivery system 20 is retracted to release coiled sheet portion 11 of stent 10 into body lumen 100, as shown in FIG. 2B. When stent 10 is released, distal-most coiled sheet portion 11 at least partially expands to engage the inside wall of the body lumen. As sheath 24 continues to be retracted proximally, helical articulation 13 unwinds from within coiled sheet portion 11 so that the articulation spans and supports stenosis 101. When sheath 24 is fully retracted, proximal coiled sheet portion 12 is deployed. A balloon element (not shown) may then be inserted within the deployed stent to activate any locking means that may be employed on either or both of the coiled sheet portions. As shown in FIG. 2C, when stent 10 is completely deployed there is little or no overlap, and little or no gap formation, between adjacent turns of the helical articulation.

Figure 3A:
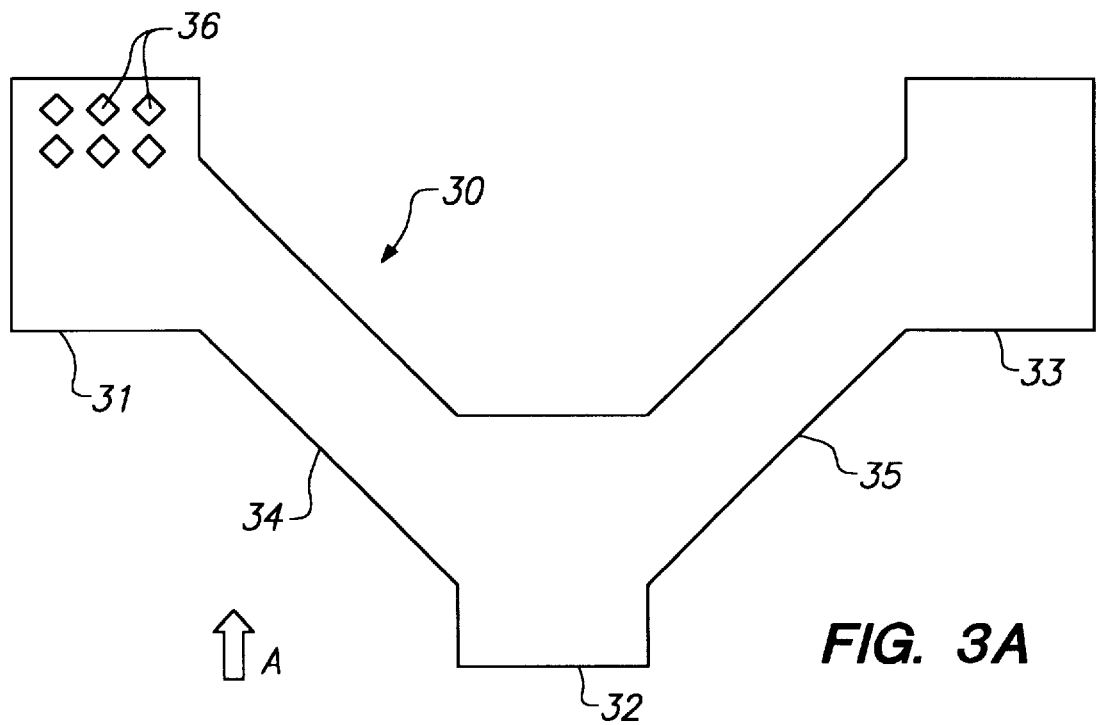
FIGS. 3A–3C are views similar to FIGS. 1A through 1C, respectively, of an alternative member of the first family of embodiments, including an intermediate coiled sheet portion.
Figure 3B:
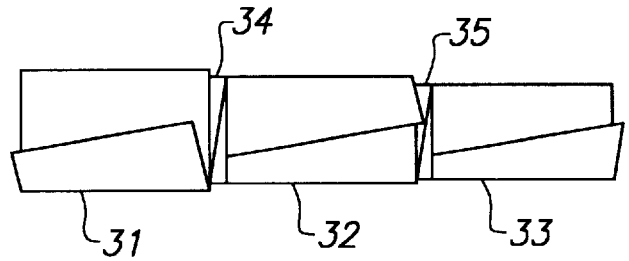
Figure 3C:
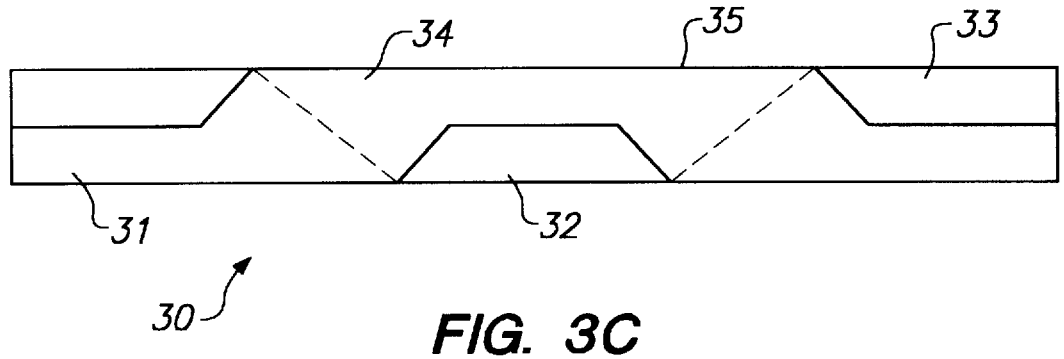

Referring now to FIGS. 3A–3C, an alternative embodiment of the first family of stents is described. Stent 30 comprises three coiled sheet portions 31, 32, and 33, and intermediate helical articulations 34 and 35. Coiled sheet portions 31–33 are similar in construction to the coiled sheet portions 11 and 12 of FIGS. 1, while helical articulations 34 and 35 are similar in construction to helical articulation 13 described above with respect to FIG. 1A. Stent 30 is formed from a thin flat sheet of resilient biocompatible material, as described hereinabove, and may include multiplicity of openings 36 in a suitable pattern for promoting tissue regrowth.

Like stent 10 of FIGS. 1, stent 30 experiences at least partial telescoping of the turns of helical articulation when the stent is rolled into a tubular shape along direction A. This telescoping of the articulated portions of the stent may reduce the overall length of the stent by up to 40% (assuming sections of equal length) as well as providing some flexibility to improve tracking of the stent through a tortuous vessel. When released to its expanded state, shown in FIG. 3C, stent 30 recovers its initial length with little or no gap formation between adjacent turns of the helical articulation.

In FIGS. 4A–4D, an alternative member of the first family of embodiments is described. Stent 40 of FIG. 4A (which is not to scale) includes first and second coiled sheet portions 41 and 42 joined at an angle a by helical mesh portion 43. Coiled sheet portion 41 includes locking teeth 44 along edge 45 that is parallel to the longitudinal axis of the stent when rolled to its tubular form. Coiled sheet portion 42 also includes one or more rows of locking teeth 46 disposed near the juncture with helical portion 43, so that locking teeth 46 project outwardly to engage coiled sheet portion 42 near free end 47 when stent 40 is rolled to its tubular form.

Figure 4B:
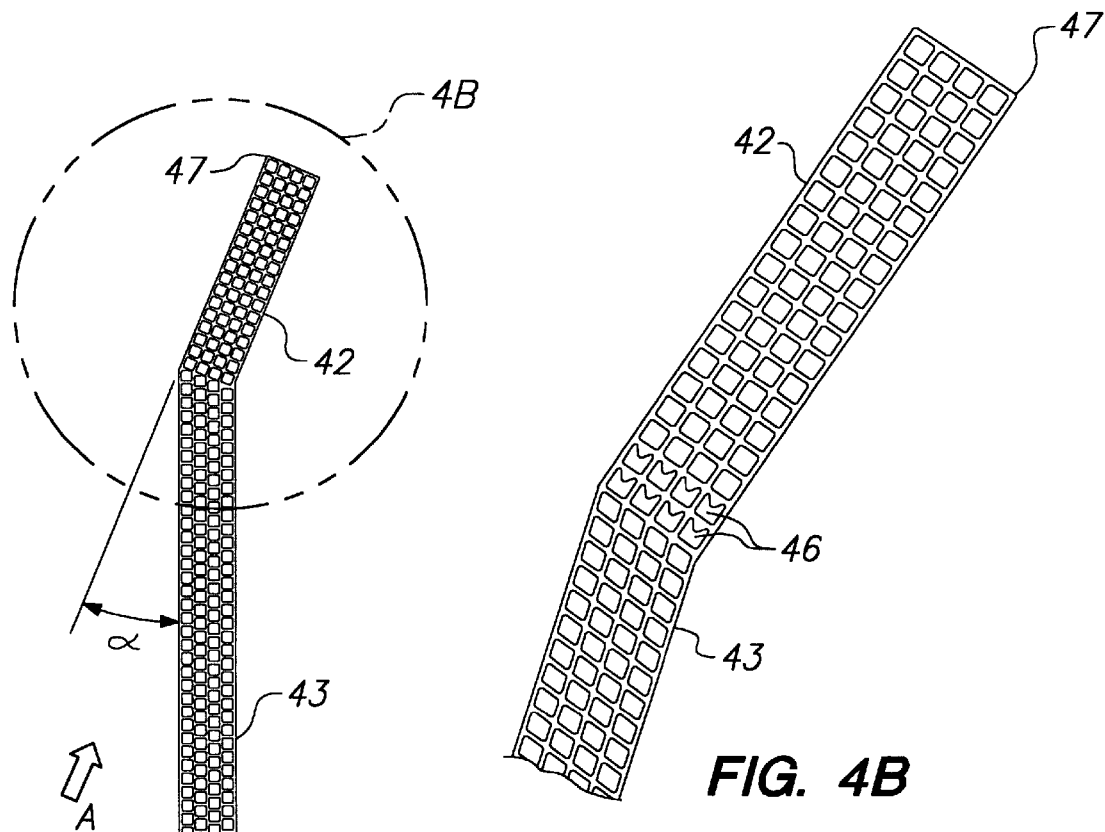
FIGS. 4A–4D are, respectively, a plan view, detailed plan views and elevation view of yet another alternative member of the first family of embodiments.
Figure 4A:
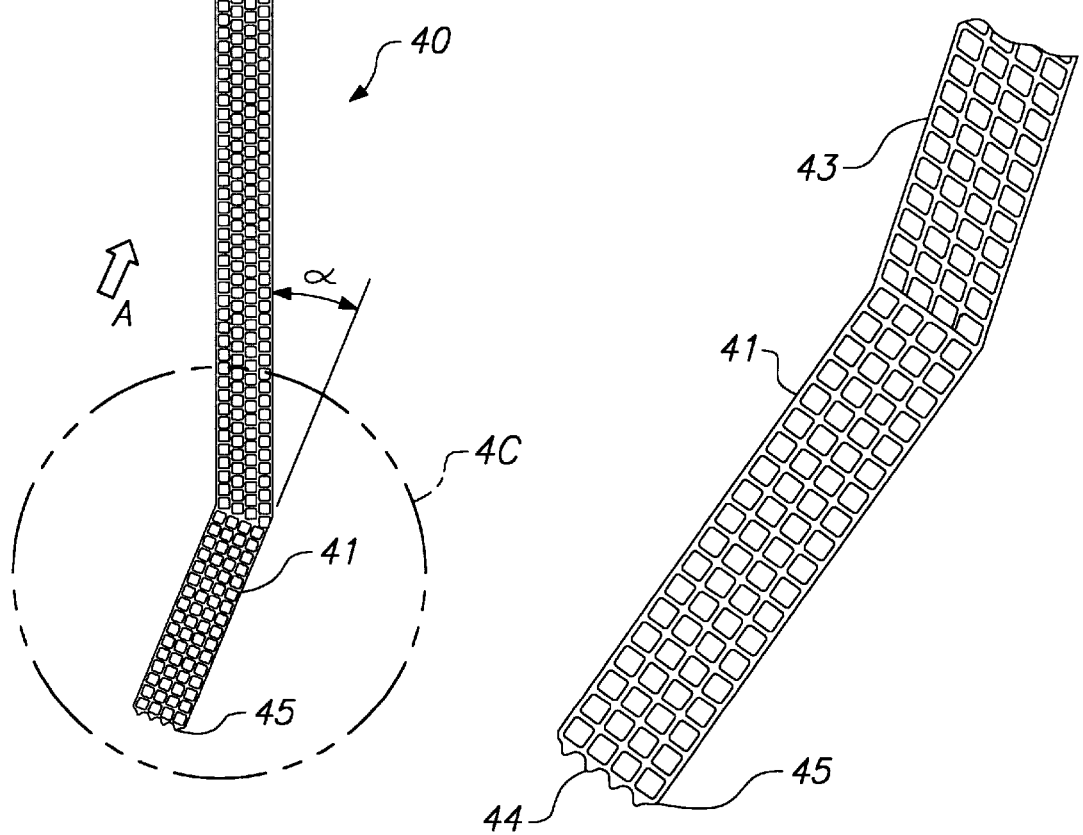
Figure 4C:
Figure 4D:
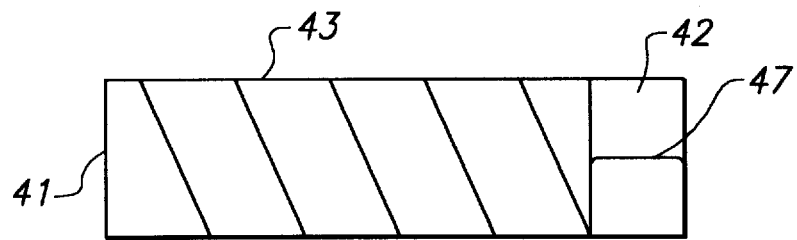

As will be apparent from the foregoing, stent 40 is rolled in direction A to form a tubular member having a side view as depicted in FIG. 4D (mesh details omitted for clarity). Stent 40 is rolled to its contracted state beginning with edge 45 and continuing through to edge 47. When in its expanded tubular form disposed within a body lumen (FIG. 4D), stent 40 is configured so that coiled sheet portion 41 is partially overlapped by helical portion 43, while locking teeth 46 of coiled sheet portion 42 engage free end 47.

Figure 5A:
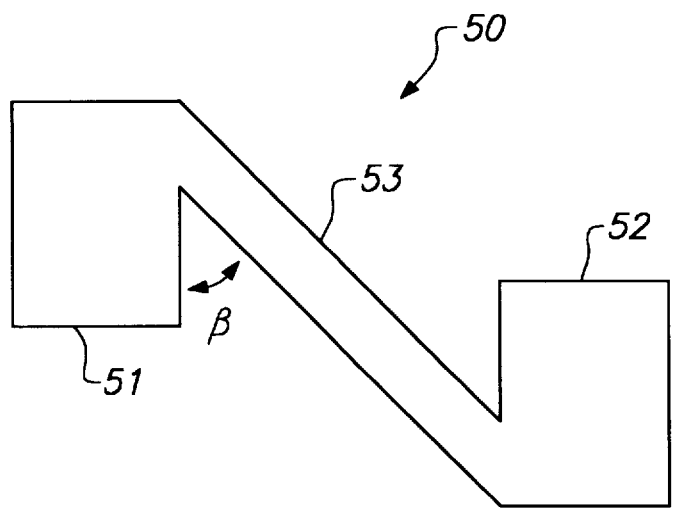
FIG. 5A is a plan view of an illustrative one of a second family of embodiments of stents constructed in accordance with the present invention.
Figure 5B:
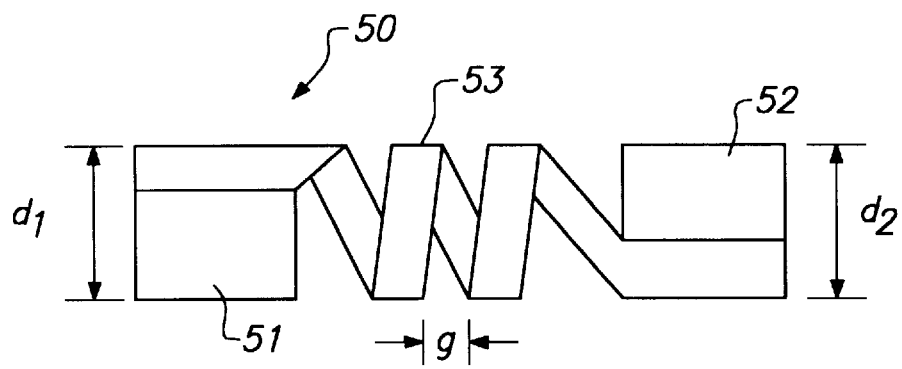
FIG. 5B is an elevation view of the stent of FIG. 5A in its expanded state.

Referring now to FIGS. 5A and 5B, stent 50 illustrative of a second family of embodiments of the present invention, is described. Stent 50 comprises coiled sheet portions 51 and 52 joined by helical articulation 53, and includes multiplicity of openings (not shown) forming a mesh pattern. Stent 50 comprises a resilient material, as described hereinabove, and may include locking elements on either or both of coiled sheet portions 51 and 52.

Helical articulation 53 of stent 50 forms an angle β with respect to coiled sheet portions 51 and 52 such that when articulation 53 is wound a desired number of turns, gaps g are formed between neighboring turns of the stent. In addition, coiled sheet portions 51 and 52 may be rolled to form frustoconical sections when in the expanded state. Thus, as seen in FIG. 5B, coiled sheet portion 51 may have diameter $d_1$ while coiled sheet portion 52 has smaller diameter $d_2$. In addition to mechanical processing, coiled sheet portions 51 and 52 may be subjected to multiple or different heat treatment processes to determine the expanded diameters of the respective portions.

Due to the looser pitch between turns of helical articulation 53, stent 50 does not exhibit the telescoping effect observed in the first family of embodiments of the present invention. Instead, when wound down to its contracted state, the gaps between adjacent turns of the helical portion are greatly reduced. Stent 50, however, remains very flexible and is expected to have good trackability characteristics.

Figure 6A:
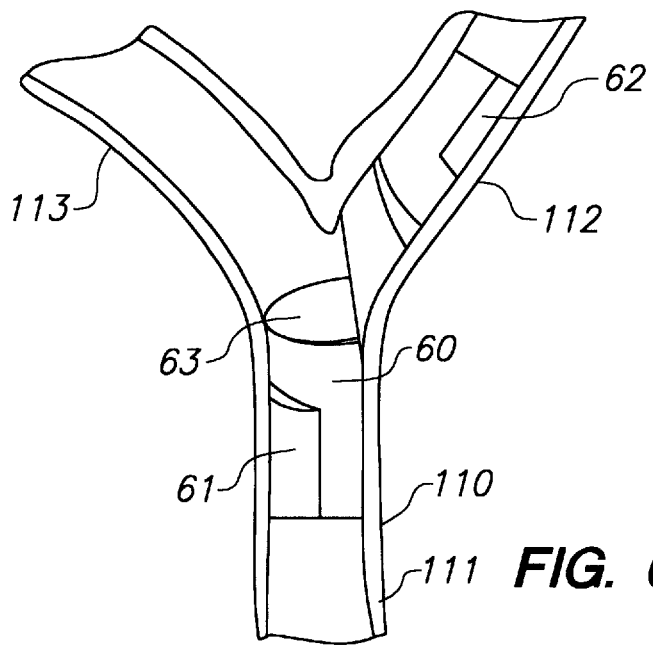
FIG. 6A is an elevation view, partly in section, of a stent similar to that of FIGS. 5 deployed in a bifurcated body lumen.

As illustrated in FIG. 6A, stent 60 constructed in accordance with the second family of embodiments of the present invention is expected to be particularly well suited for use in supporting a bifurcated region of body lumen 110. Stent 60 comprises coiled sheet portions 61 and 62 joined by helical articulation 63. Coiled sheet portion 61 is disposed in common lumen 111, while coiled sheet portion 62 is disposed in branch 112, with helical articulation 113 spanning and supporting the bifurcated region. Stent 60 is placed within the common lumen 111 and branch 112 so that the gap created by bending the coiled sheet portions relative to one another faces the opening to the branch 113. In this manner, a stenosis near the bifurcation region can be treated despite the presence of relatively little straight lumen on either side of the bifurcated region.

Figure 6B:
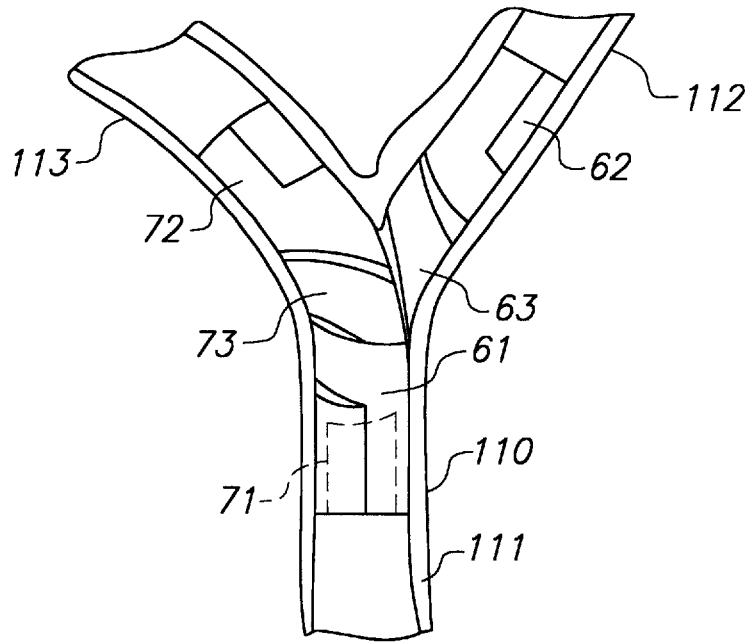
FIG. 6B is an elevation view, partly in section, of the bifurcated lumen of FIG. 6A after deployment of a second nested stent.

With respect to FIG. 6B, stent 70 comprising coiled sheet portions 71 and 72 and helical articulation 73 is disposed in the bifurcated body lumen 110 so that coiled sheet portion 71 is nested within coiled sheet portion 61 of stent 60, and coiled sheet portion 72 is disposed in branch 113. In this manner, helical articulation 73 spans and further supports the bifurcated region of body lumen 110. To enhance nesting of coiled sheet portions 61 and 71 of stents 60 and 70, respectively, those coiled sheet portions may be made of reduced thickness, for example, by etching, to reduce the combined thickness of the stents when nested.

While preferred illustrative embodiments of the present invention are described above, it will be apparent to one skilled in the art that various changes and modifications may be made therein without departing from the invention, and it is intended in the appended claims to cover all such changes and modifications which fall within the true spirit and scope of the invention.

What is claimed is:

1. A stent for supporting a body lumen, the stent comprising:

resilient first and second coiled sheet portions, each of the first and second coiled sheet portions being concentrically coiled;

a helical articulation joining the first and second coiled sheet portions;

wherein the stent has a first diameter suitable for transluminal delivery when in a contracted state and a second larger diameter when deployed.

2. The stent as defined in claim 1 wherein the helical articulation comprises a plurality of turns, the helical articulation having a pitch sufficient to prevent formation of gaps between the plurality of turns when the stent is deployed.

3. The stent as defined in claim 2 wherein the helical articulation partially telescopes within one of the first and second coiled sheet portions when the stent is wound to the contracted state.

4. The stent as defined in claim 1 wherein the first coiled sheet portion has a tapered outer diameter when deployed.

5. The stent as defined in claim 1 wherein one of the first and second coiled sheet portions and the helical articulation have a multiplicity of openings.

6. The stent as defined in claim 1 wherein the first and second coiled sheet portions have equal lengths.

7. The stent as defined in claim 1 wherein the first and second coiled sheet portions have equal diameters.

8. The stent as defined in claim 1 wherein the first and second coiled sheet portions have equal thicknesses.

9. The stent as defined in claim 1 wherein the first coiled sheet portion and the helical articulation have equal lengths when the stent is deployed.

10. The stent as defined in claim 1 wherein at least one of the first and second coiled sheet portions includes locking elements to retain the stent at the second diameter.

11. The stent as defined in claim 1 wherein the stent comprises a nickel-titanium alloy.

12. The stent as defined in claim 1 for treating a bifurcation:

wherein the first and second coiled sheet portions and the helical articulation form a first member, the first coiled sheet portion adapted for disposition in a common lumen of the bifurcation, the second coiled sheet portion adapted for disposition in a first branch of the bifurcation; the stent further comprising a second member comprising a third coiled sheet portion, a fourth coiled sheet portion, and a helical articulation disposed therebetween, the third coiled sheet portion adapted for disposition in the common lumen of the bifurcation nested within the first coiled sheet portion of the first member, the fourth coiled sheet portion adapted for disposition in a second branch of the bifurcation.

13. The prosthesis as defined in claim 12 wherein at least one of the first through fourth coiled sheet portions and the helical articulations have a multiplicity of openings.

14. The prosthesis as defined in claim 12 wherein at least two of the first through fourth coiled sheet portions have equal lengths.

15. The prosthesis as defined in claim 12 wherein at least two of the first through fourth coiled sheet portions have equal diameters.

16. The prosthesis as defined in claim 12 wherein the first and third coiled sheet portions have smaller thicknesses than the second and fourth coiled sheet portions.

17. The prosthesis as defined in claim 12 wherein at least one of the first through fourth coiled sheet portions includes locking elements.

18. The prosthesis as defined in claim 12 wherein the first and second members have unequal lengths.

19. The prosthesis as defined in claim 12 wherein the first and second members comprise a nickel-titanium alloy.

20. A stent for supporting a body lumen, the stent comprising:
  a resilient first coiled sheet portion having a first length, a first thickness, and a first range of expanded diameters, the first coiled sheet portion being concentrically coiled;
  a resilient second coiled sheet portion having a second length, a second thickness, and a second range of expanded diameters, the second coiled sheet portion being concentrically coiled;
  a helical articulation joining the first and second coiled sheet portions;
  wherein the stent has a contracted state suitable for transluminal delivery and an expanded state when deployed.

21. The stent as defined in claim 20 wherein the helical articulation comprises a plurality of turns, the helical articulation having a pitch sufficient to prevent formation of gaps between the plurality of turns when the stent is in the expanded state.

22. The stent as defined in claim 21 wherein the helical articulation partially telescopes within one of the first and second coiled sheet portions when the stent is wound to the contracted state.

23. The stent as defined in claim 20 wherein the first coiled sheet portion has a tapered outer diameter when deployed.

24. The stent as defined in claim 20 wherein one of the first and second coiled sheet portions and the helical articulation have a multiplicity of openings.

25. The stent as defined in claim 20 wherein the first and second lengths are unequal.

26. The stent as defined in claim 20 wherein the first and second ranges of expanded diameters are unequal.

27. The stent as defined in claim 20 wherein the first and second thicknesses are unequal.

28. The stent as defined in claim 20 wherein the first coiled sheet portion and the helical articulation have unequal lengths when the stent is deployed.

29. The stent as defined in claim 20 wherein the first coiled sheet portion includes locking elements to retain the first coiled sheet portion at a selected expanded diameter.

30. The stent as defined in claim 20 wherein the stent comprises a nickel-titanium alloy.

* * * * *